US00RE35747E

United States Patent [19]

Penman et al.

[11] E Patent Number: Re. 35,747

[45] **Reissued Date of Patent: *Mar. 17, 1998**

[54] METHOD FOR DETERMINING TISSUE OF ORIGIN AND PRESENCE AND EXTENT OF CELLULAR ABNORMALITIES

[75] Inventors: Sheldon Penman, Brookline; Edward G. Fey, Boston, both of Mass.

[73] Assignee: Massachusetts Institute of Technology, Cambridge, Mass.

[ * ] Notice: The portion of the term of this patent subsequent to Nov. 21, 2006, has been disclaimed.

[21] Appl. No.: 794,586

[22] Filed: Nov. 19, 1991

Related U.S. Patent Documents

Reissue of:

[64] Patent No.: 4,885,236
Issued: Dec. 5, 1989
Appl. No.: 946,770
Filed: Dec. 23, 1986

U.S. Applications:

[63] Continuation-in-part of Ser. No. 812,955, Dec. 24, 1985, Pat. No. 4,882,268.

[51] Int. Cl.[6] ..... C12Q 1/68; C12Q 1/02; G01N 33/53; C07G 15/00

[52] U.S. Cl. ..... 435/6; 435/7.21; 435/7.23; 435/29; 435/264; 435/268; 435/269; 435/270; 435/272; 436/63; 436/64; 436/548; 530/350; 530/358; 530/389.1; 530/412; 530/420; 536/24.2; 935/78

[58] Field of Search ..... 435/7.23, 7.21, 435/6, 29, 264, 268, 269, 270, 272; 436/63, 64, 548; 530/358, 389.1, 1, 412, 350, 387.7, 389.7; 536/27

[56] References Cited

U.S. PATENT DOCUMENTS

| | | | |
|---|---|---|---|
| 4,358,535 | 11/1982 | Falkow | 435/5 |
| 4,569,916 | 2/1986 | Penman | 436/64 |
| 4,882,268 | 11/1989 | Penman et al. | 435/5 |

OTHER PUBLICATIONS

Lydersen, et al., Cell, vol. 22, pp. 482–499 (1980).
Anderson et al., *Clin. Chem.*, 30:1898–1905 (1984).
Barrack et al., *Recent Progress in Hormone Research*, Roy O. Greep, ed., vol. 38, pp. 133–137, and 180–189 (Academic Press, New York, 1982).
Barrack et al., *J. Biol. Chem.*, 255:7265–7275 (1980).
Berezney et al., *J. Cell Biol.*, 73:616–637 (1977).
Berezney et al., *Science*, 189:291–293 (1975).
Berezney, *J. Cell Biol.*, 85:641–650 (1980).
Bhorjee et al., *J. Cell Biol.*, 97:389–396 (1983).
Bludau et al., *Exper. Cell Res.*, 165:269–282 (1986).
Bodnar et al., *Mol. Cell Biol.*, 3:1567–1579 (1983).
Briggs et al., *J. Cell. Biochem.*, 21:249–262 (1983).
Burdon et al., *Biochem. Biophys. Acta.*, 825:70–79 (1985).
Buttyan et al., *J. Biol. Chem.*, 258:14366–14370 (1983).
Caizergues–Ferrer et al., *Biochem. Biophys. Res. Com.*, 118:444–450 (1984).
Capco et al., *Cell*, 29:847–858 (1982).
Chaly et al., *Can. J. Biochem. Cell Biol.*, 63:644–653 (1985).
Chaly et al., *Cell Biol. Inter. Reports*, 10:421–428 (1986).
Chaly et al., *J. Cell Biol.*, 99:661–671 (1984).
Chem. Abstracts, 99, No. 192945A, Hapbets et al., *Clin. Exp. Immunol.*, 54:265–276 (1983).
Chem. Abstracts, 101, No. 19258R, Zbarskii et al., *Macromol. Funct. Cell*, 1:114–123 (1980).
Chiu et al., *Rad. Res.*, 107:24–38 (1986).
Coffey et al., *Adv. Enzyme Regul.*, 17:213–248 (1978).
Coffey et al., *Adv. Enzyme Regul.*, 14:63–100 (1976).
Comings et al., *Exp. Cell Res.*, 103:341–360 (1976).
Detke et al., *J. Biol. Chem.*, 257:3905–3911 (1982).
Eastment et al., *Blood*, 57:747–757 (1981).
Eisenman et al., *Mol. Cell. Biol.*, 5:114–126 (1985).
Fey et al., *J. Cell Biol.*, 99:203s–208s (1984).
Fry et al., *Proc. Natl. Acad. Sci. USA*, 81:4409–4413 (1984).
Fey et al., *J. Cell Biol.*, 102:1654–1665 (1986).
Fey et al., *J. Cell Biol.*, 98:1973–1984 (1984).
Fisher et al., *J. Cell Biol.*, 92:674–686 (1982).
Flickinger, *Cell Biol. Intetnat. Reports*, 10:415–420 (1986).
Franklin et al., *J. Cell. Biochem.*, 24:1–14 (1984).
Hentzen et al., *Proc. Nat'l . Acad. Sci. USA*, 81:304–307 (1984).
Hodge et al., *J. Cell. Biol.*, 72:194–208 (1977).
Intres et al., *In Vitro Cell Dev. Biol.*, 21:641–648 (1985).
Kaufmann et al., *Exp. Cell Res.*, 132:105–123 (1981).
Kaufmann et al., *Exp. Cell Res.*, 155:477–495 (1984).
Kirsch et al., *Biochem. Biophys. Res. Comm.*, 137:640–648 (1986).

(List continued on next page.)

*Primary Examiner*—Toni R. Scheiner
*Attorney, Agent, or Firm*—Testa, Hurwitz & Thibeault

[57] ABSTRACT

A biochemical procedure for identification and characterization of cells in a biopsy or sample of a body fluid. The method can be used to determine cell type, i.e. epidermal, neuronal; tissue of origin, i.e. breast tissue, liver tissue; and degree of abnormality. The procedure can also be used to make antibodies and hybridization probes to detect cell or tissue specific antigens and nuclear matrix associated nucleic acids in cellular material and body fluids.

The procedure is based on the isolation and analysis of the components of a specific subcellular protein fraction referred to here as the "nuclear matrix". The nuclear matrix includes proteins and nuclear matrix associated DNA specific to different cell types. These proteins and nucleic acids are altered or new ones expressed as a result of viral infection, genetic defects or malignancy.

The method has a number of important clinical applications in determining tissue type, tissue of origin, degree of malignancy and extent of metastasis in cancer patients; in detecting and analyzing chromosomal deficiencies or genetic defects, especially in cells obtained by amniocentesis; in identifying viral or other infections; and in measuring the extent and location of cell damage, particularly in patients with localized cell damage or autoimmune disease. The isolated nuclear matrix proteins are also useful in screening for drugs binding to and affecting the nuclear matrix.

23 Claims, 5 Drawing Sheets

OTHER PUBLICATIONS

Lehner et al., *Exp. Cell Res.*, 162:205–219 (1986).
Long et al., *Cell*, 18;1079–1090 (1979).
Long et al., *Biol. Cell*, 48:99–108 (1983).
MacDonald et al., *Biochem. Biophys. Res. Comm.*, 138:254–260 (1986).
Martelli et al., *J. Cell Biol.*, 103:181 (1986).
Milavetz et al., *Virology*, 134:406–420 (1984).
Milavetz et al., *J. Cell. Physiol.*, 127:358–396 (1986).
Moy et al., *Cancer Res.*, 46:4672–4676 (1986).
Mullenders et al., *Biochim. Biophys. Acta.*, 698:70–77 (1982).
O'Farrell, *J. Biol. Chem.*, 10:4007–4021 (1975).
O'Farrell et al., *J. Cell Sci.*, 82:173–186 (1986).
Peters et al., *J. Cell Biol.*, 86:135–155 (1980).
Peters et al., *Eur. J. Biochem.*, 129:221–232 (1982).
Pienta et al., *J. Cell Sci. Suppl.*, 1:123–125 (1984).
Reiter et al., *J. Cell Sci.*, 76:17–33 (1985).
Schmidt et al., *Cancer Res.*, 44:5291–5304 (1984).
Shelton et al., *J. Biol. Chem.*, 255:10978–10983 (1980).
Simmen et al., *Endocrinology*, 115:1153–1197 (1984).
Simmen et al., *J. Cell Biol.*, 99:588–593 (1984).
Smith et al., *Mol. Cell. Biochem.*, 70:151–168 (1986).
Song et al., *J. Biol. Chem.*, 258:3309–3318 (1983).
Stastny et al., *Clin. Chem.*, 30:1914–1918 (1984).
Staufenbiel et al., *Eur. J. Cell Biol.*, 31:341–348 (1983).
Staufenbiel et al., *J. Cell Biol.*, 98:1866–1894 (1984).
Todorova et al., *Biochem. Biophys. Acta.*, 783:36–41 (1984).
Van der Velden et al., *Biochim. Biophys. Acta.*, 782:429–436 (1984).
Van Ekelen et al., *Exp. Cell Res.*, 141:181–190 (1982).
Van Eekelen et al., *J. Cell Biol.*, 88:554–563 (1981).
Verheijen et al., *J. Cell Bol.*, 103:179 (1986).
Verheijen et al., *J. Cell Sci.*, 80:103–122 (1986).
Werner et al., Exp. Cell Res., 151:384–395 (1984).
Wojtkowiak et al., *Cancer Res.*, 42:4546–4552 (1982).
Wu et al., *Cancer Research*, 41:336–342 (1981).

METHOD FOR DETERMINING TISSUE OF ORIGIN AND PRESENCE AND EXTENT OF CELLULAR ABNORMALITIES

Matter enclosed in heavy brackets [ ] appears in the original patent but forms no part of this reissue specification; matter printed in italics indicates the additions made by reissue.

REFERENCE TO RELATED APPLICATION

This application is a continuation-in-part of our copending U.S. patent application Ser. No. 812,955, filed Dec. 24, 1985, *now U.S. Pat. No. 4,882,268,* entitled "Method for Determining Tissue of Origin and Degree of Malignancy of Tumor Cells".

BACKGROUND OF THE INVENTION

The U.S. Government has certain rights in this invention by virtue of National Institute of Health Grant Numbers 5R01 CA08416-20 and 1R01CA37330-01 and National Science Foundation Grant Number PCM 8309334.

Diagnosis of viral infection, cancer, chromosomal defects or autoimmune disease is often difficult and inexact. Heretofore, determining the properties of tumor cells or other abnormal cells has been the province of the clinical pathologist. Diagnosis is generally based on the morphology of the cells in histological preparations. Such diagnosis has serious limitations and cannot always distinguish tumor type and tissue of origin. There is a great need for alternative means of identifying cell type and stage of malignancy or abnormality. Chromosomal defects can be detected only in the case of gross morphological defects or where the proteins encoded by the missing or defective genes are known and can be assayed for. Viral infections can usually be diagnosed only by measuring antibody levels, examination of cells, and presence of clinical symptoms.

There is also a need for a means of identifying the site of tissue damage, not only in autoimmune diseases where the target cell is known, but also, for example, in bladder infection or myocardial infarction, where cell degradation products might be released into the urine or bloodstream.

Attempts have been made to determine cell type by analysis of the protein composition of whole cell extracts. However, these extracts contain a number of different proteins, of which the vast majority do not vary between cell types. Even with techniques providing increased resolution between proteins, such as the more recent methods of two dimensional gel electrophoresis, such efforts have largely failed to find meaningful differences in proteins that could reliably serve as a basis for cell and tissue type identification. Even where there might be a change in proteins due to infection or malignancy, existing methods fail to differentiate the new or altered proteins from background proteins.

All cells, both plant and animal, have a nucleus surrounded by the cell cytoplasm. The nucleus contains the cellular DNA complexed with protein and termed chromatin. The chromatin, with its associated proteins, constitutes the major portion of the nuclear mass. The chromatin is organized by the internal skeleton of the nucleus, referred to here as the nuclear matrix. Although it is known that the nuclear matrix contains cell-type specific proteins and a small percentage of the total DNA, current electron microscopy techniques do not image the matrix and there are no reliable methods of separating specific non-chromatin matrix proteins from the much larger quantity of chromatin proteins. The methods that have been used either separated out the soluble proteins and discarded the insoluble proteins, or used high salt (2M NaCl or 2M LiCl) and other harsh solvents to extract these nuclear matrix proteins.

There has been limited success in biochemically identifying cells by analyzing the protein composition of a subcellular fraction consisting of the intermediate filaments. The intermediate filaments are proteins present in all cells and can be used to discriminate between five major classes of cells: epithelial, neuronal, glial, muscle and mesenchymal cells such as fibroblasts. Labeled antibodies to these proteins only serve to distinguish among these broad cell classes, although some further discrimination is possible with epithelial cells. In epithelial cells, the intermediate filaments, the cytokeratins, are complex and differ between many types of epithelia. However, the cytokeratins can only be specifically distinguished chemically: antibodies have so far proven unable to discriminate precisely among more than a few of the cytokeratins. There are also reports that the cytokeratins are altered in some malignancies making their use for fine discrimination uncertain.

It is therefore an object of the present invention to provide a method for determining tissues of origin and stages of abnormality of tumor cells, virally transformed cells, and genetically defective or deficient cells.

It is another object of the present invention to provide a method for specifically identifying the tissue of origin and extent of tissue injury in disease states involving cellular destruction, including autoimmune diseases, myocardial infarction, and bacterial infection.

It is a further object of the invention to provide a method which can be performed relatively easily and quickly.

It is a still further object of the invention to provide a method for analyzing tissue of origin which is highly reproducible, objective and can be standardized.

It is yet another object of the present invention to provide biochemical methods including antibodies and hybridization probes for isolation and analysis of cell or tissue specific nuclear matrix proteins and nuclear matrix associated DNA with much greater resolution than previous methods.

SUMMARY OF THE INVENTION

A procedure for analyzing tissue of origin and state of abnormality of genetically defective or deficient cells, virally infected cells, or tumor cells with far greater discrimination than previous methods of identification. The procedure also provides a means for identifying or imaging the tissue of origin and degree of cell damage in disease states causing cellular destruction and release of degradation products into body fluids, including autoimmune diseases.

In one embodiment of the method of the present invention, the cell nucleus is isolated, the cytoskeleton proteins and chromatin removed, the nuclear matrix isolated, and the "interior" and "exterior" components of the nuclear matrix separated. The "nuclear matrix", a specific fraction of cell protein constituting less than five percent of the total protein and six percent of the total DNA of the cell, contains many proteins that differ according to cell type and is highly enriched with cell type-specific antigens including highly cell type- and transformation-specific proteins that cannot be detected using prior art procedures. The method makes use of the unique properties of the nuclear matrix to achieve complete separation from all other cell constituents. The method is simple, rapid, reproducible, achieves a high degree of matrix purity, is applicable to essentially all types of cells, does not disrupt matrix morphology, and yields most of the biochemically significant matrix components.

The method for isolating the nuclear matrix proteins is summarized as follows:

1. Isolation and separation of cells.
2. Separation of soluble cell proteins from the nucleus and cytoskeleton by extraction of membrane lipids and soluble proteins with a non-ionic detergent-physiological salt solution.
3. Separation of cytoskeleton proteins from the nucleus by solubilization of the insoluble cell material from step 2 in either 0.25M ammonium sulfate pH 6.8, a detergent-sodium deoxycholate solution, or other gentle extraction buffer.
4. Separation of chromatin from the nuclear matrix by digestion of the insoluble material from step 3 with DNAase I and RNAase in a physiological buffer and elution of the DNA-containing nucleosomes with 0.25M ammonium sulfate solution buffered to pH 6.8 or other gentle extraction buffer.
5. Separation of the "interior" and "exterior" nuclear matrix proteins by dissolution of the insoluble material from step 4 in a buffer containing between 5 and 10M urea, preferably 8M urea, or other suitable solubilizing agent, and aggregation of the exterior proteins by dialysis into physiological buffer.

Further purification of the fraction selectively enriched in the "interior" and "exterior" proteins can be performed using HPLC, FPLC, chromatofocusing, and other methods known to those skilled in the art.

In a variation of this procedure, the cytoskeleton proteins and chromatin are removed together by digesting the insoluble material from step 2 with DNAase and RNAase, then extracting with 0.25M ammonium sulfate at pH 6.8.

In another embodiment of the method, the nuclear matrix associated DNA is isolated and analyzed, alone or in conjunction with the nuclear matrix proteins. The method consists of treating the insoluble material from step 2 with DNAase then 0.25 M ammonium sulfate at physiological pH to remove the chromatin. A phenol extraction and/or centrifugation in $CsCl_2$ is then performed to remove any remaining protein. In a variation of this method, the insoluble material from step 2 is digested with a restriction enzyme in the appropriate buffer, the chromatin extracted with 0.25M ammonium sulfate pH 6.8, then any remaining protein removed by phenol extraction and/or centrifugation in $CsCl_2$.

Because of the degree of matrix purification obtained with this procedure, several previously unknown properties of the nuclear matrix proteins have been discovered which are useful in the clinical diagnosis of tumor cells, virally infected cells, cells having chromosomal defects or genetic deficiencies, or with diseases involving specific cell damage such as autoimmune disease. The composition of the matrix proteins is different in every cell type and is further changed when the cell is transformed to the neoplastic state or has genetic aberrations. These proteins can be used to:

1. Identify general cell type (e.g., epithelial, neuronal, etc.).
2. Identify specific cell type (e.g., colon epithelium, breast epithelium, etc.). This allows identification of the origin of metastasis or site of cell damage.
3. Supply pure antigens to be employed to produce tissue specific antibodies for use in immunoassays and in diagnosis and treatment of various diseases, wherein the antibodies can be conjugated with radioactive material, nuclear magnetic resonance contrast agents, boron derivatives, or biologically active agents.
4. Determine the nature and degree of malignancy, genetic deficiency or defect, or disease.
5. Screen drugs and other agents or compounds for binding to nuclear matrix proteins, including steroid receptors.
6. Identify DNA binding sites which may alter and regulate gene expression and cell differentiation. Further characterization is achieved by analyzing and comparing the nuclear matrix associated DNA and, in particular, the restriction endonuclease fragments of nuclear matrix associated DNA. Hybridization probes can be prepared from the isolated, synthesized or cloned DNA which may be employed in a variety of assays for cell type, tissue of origin, malignancy, infection, or genetic abnormality.

Figure 1:
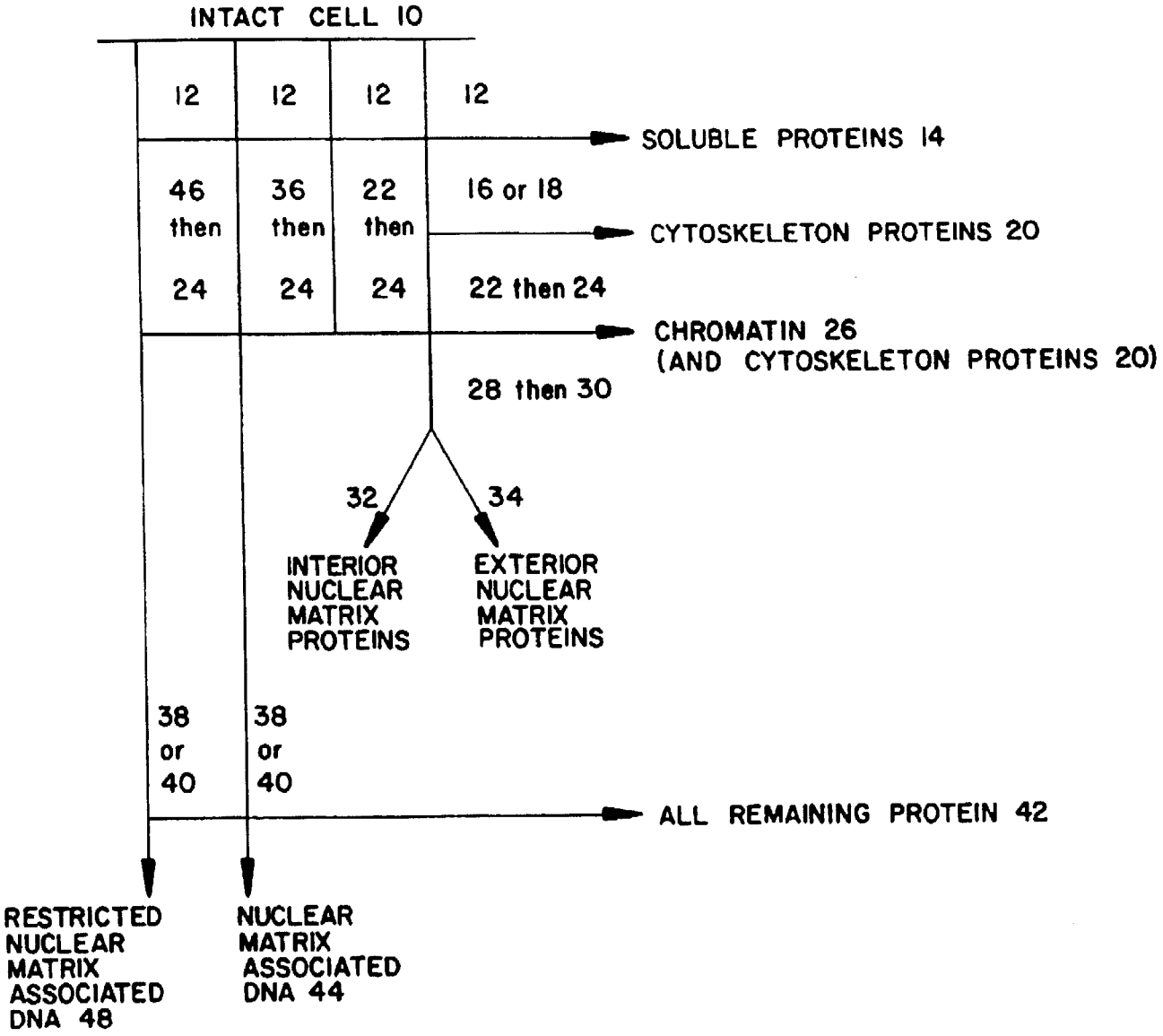
FIG. 1 is a schematic of the isolation and analysis of nuclear matrix proteins and associated DNA according to the present invention.
Figure 2A:
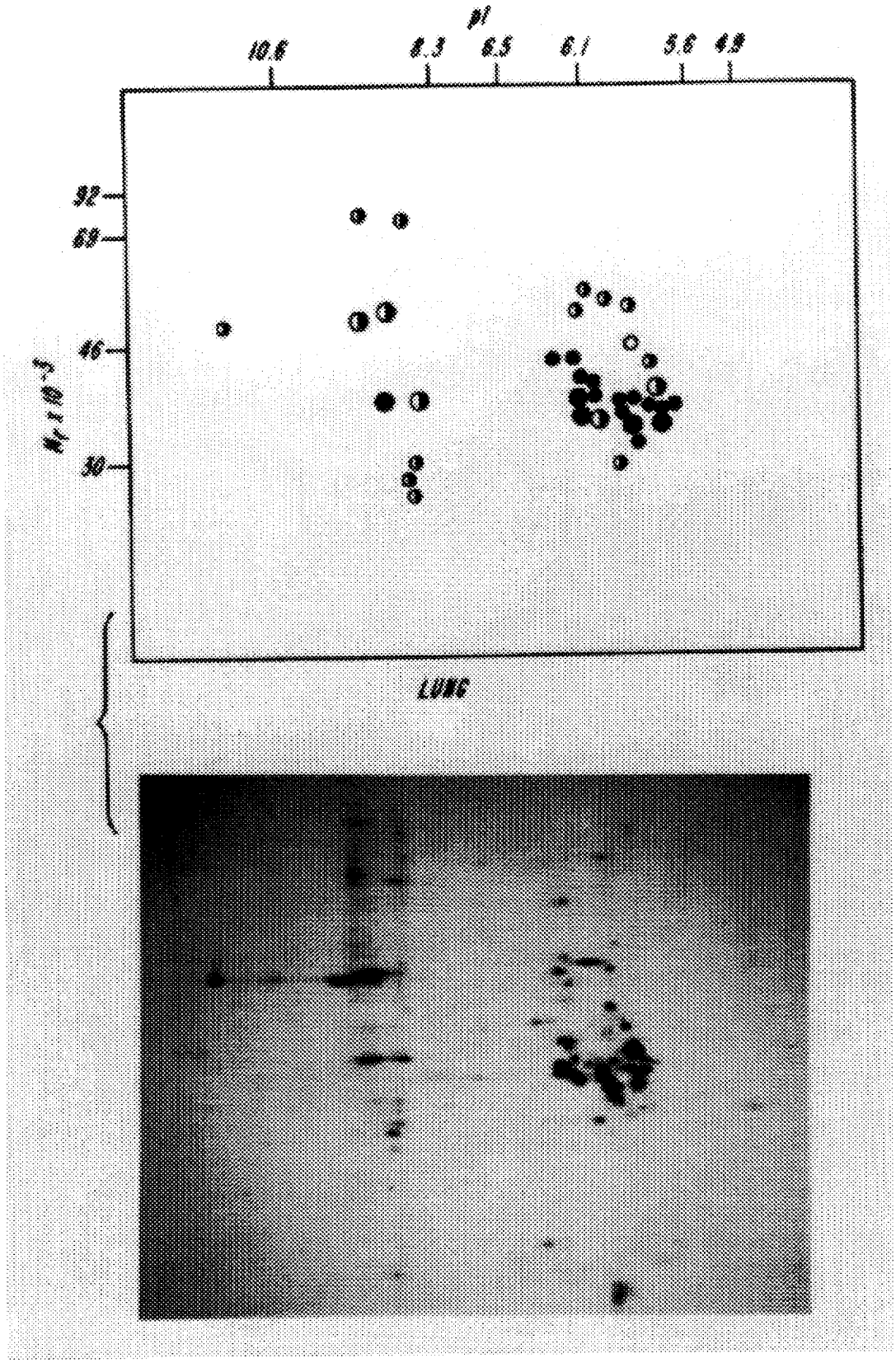
Figure 2B:
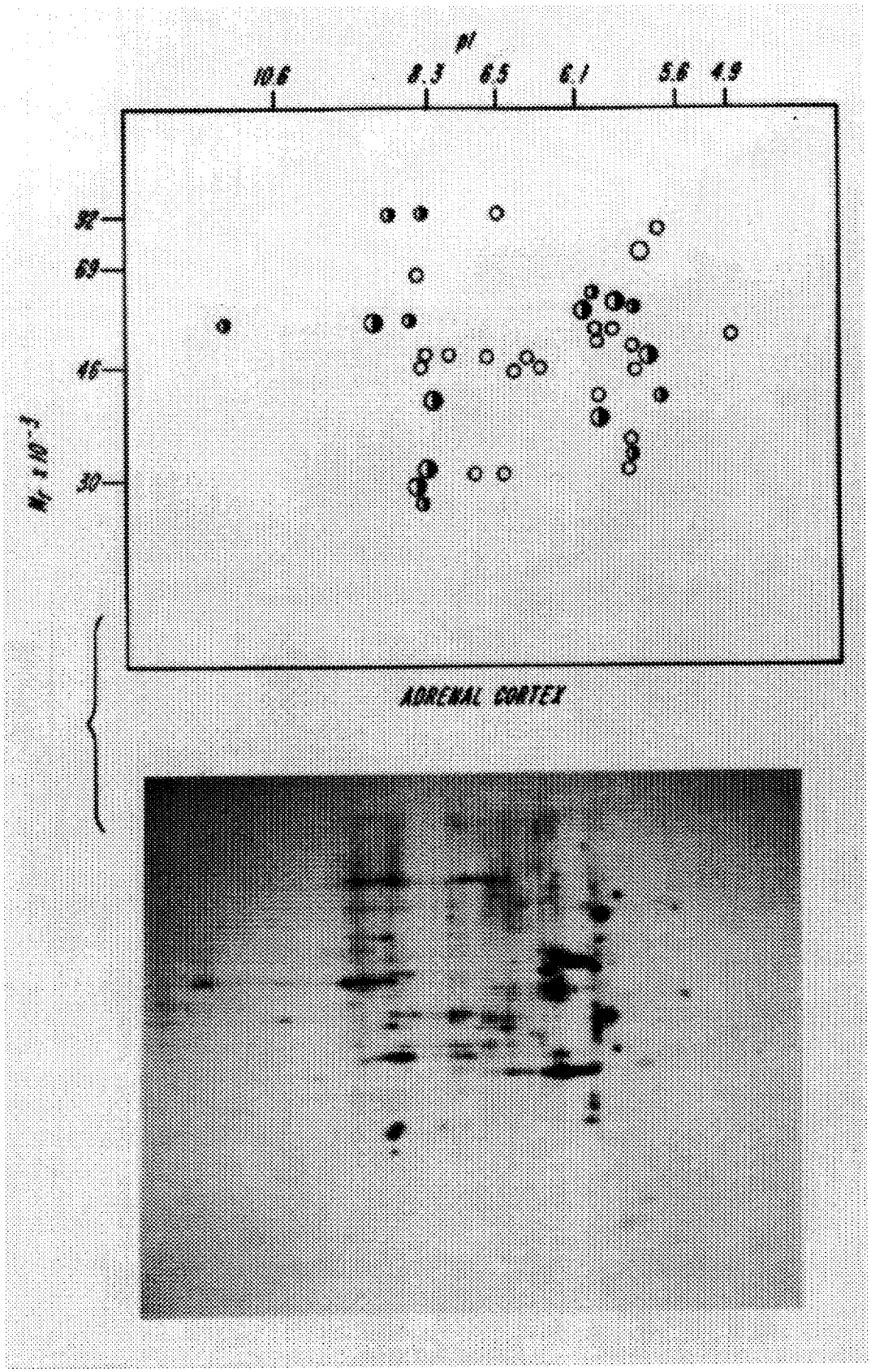
Figure 2C:
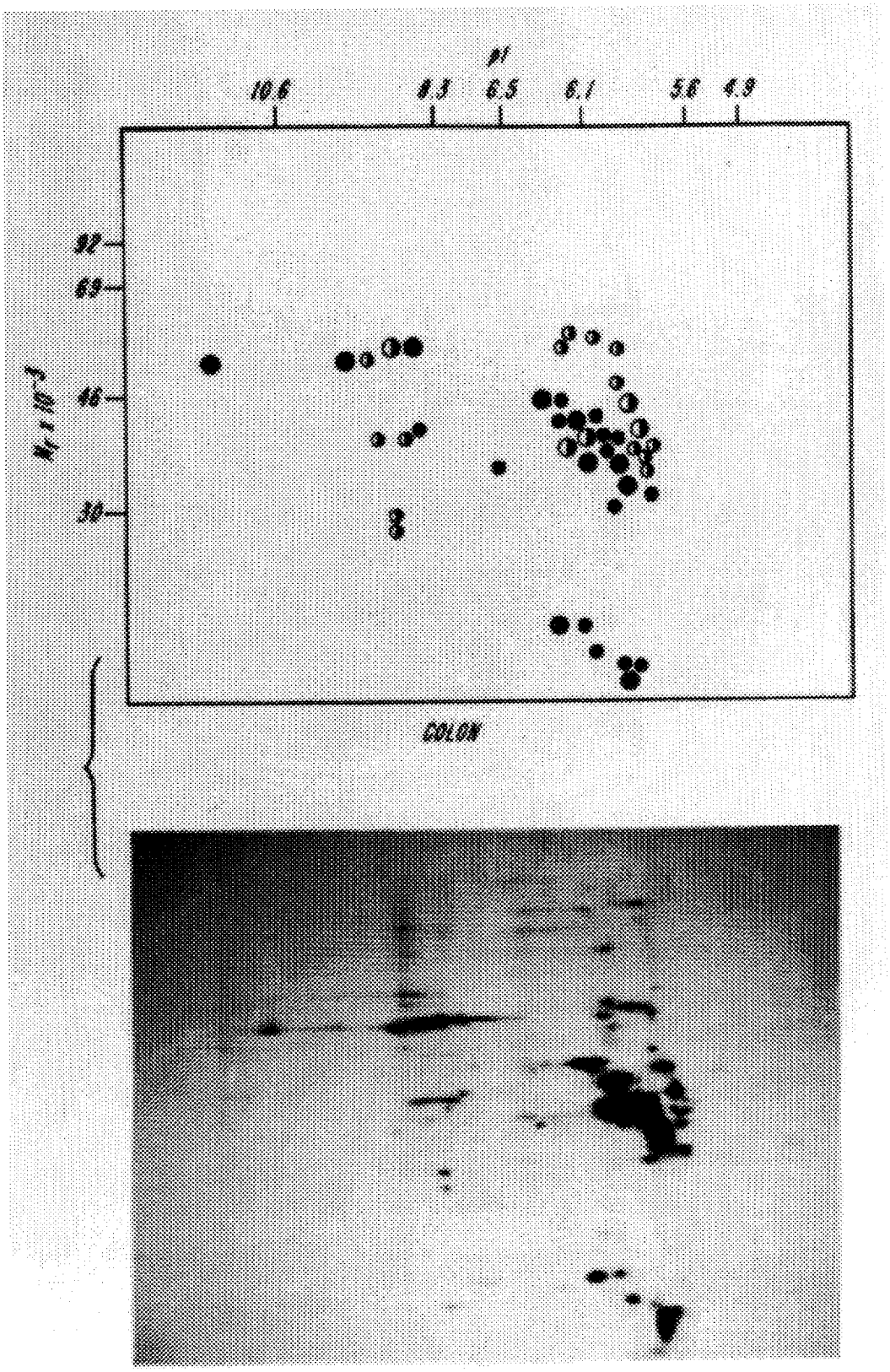
Figure 2D:
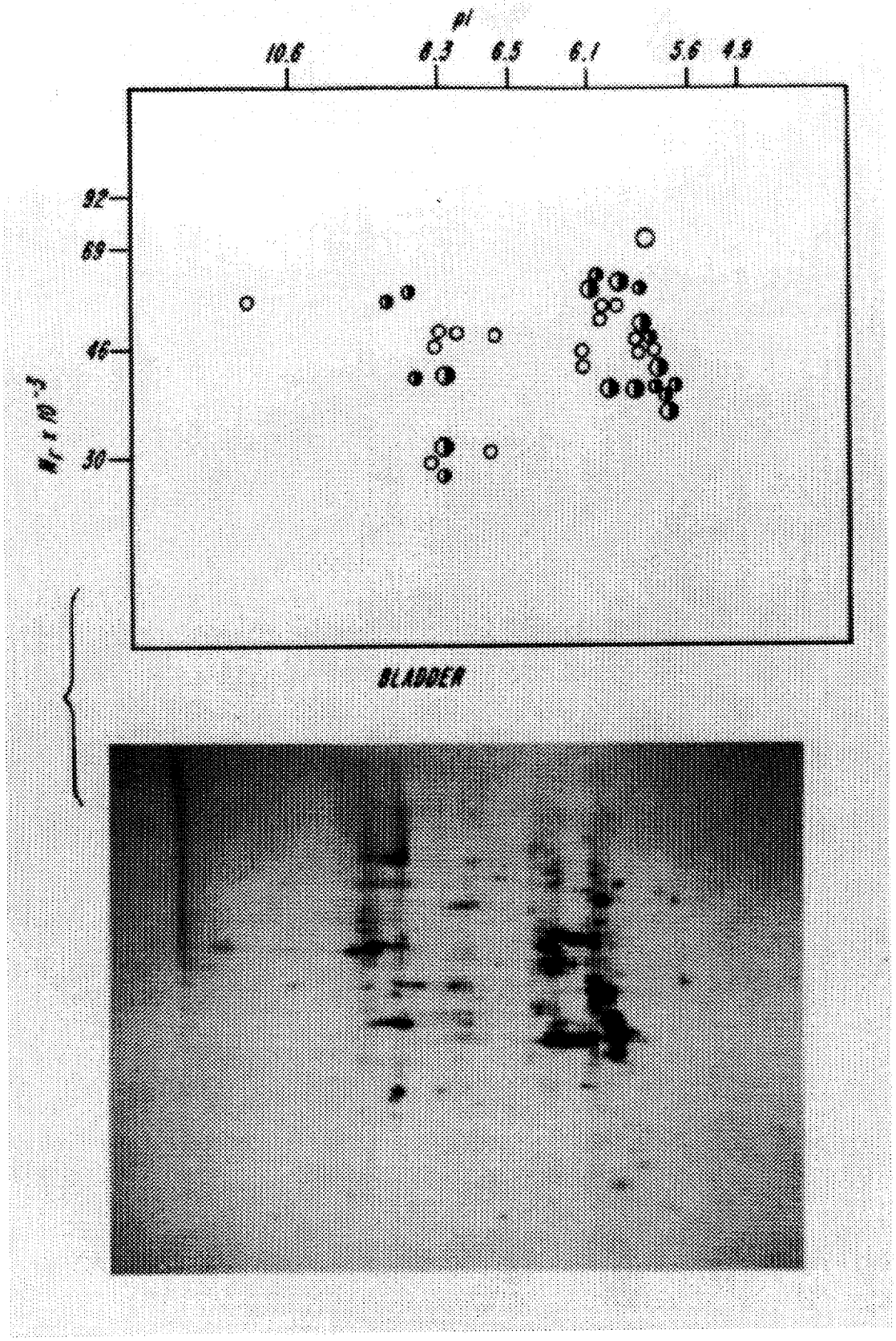

FIGS. [2a] *2A* and [2a'] *2B* are a comparison of two dimensional electropherograms (pI vs. m.w.), both actual and diagrammatic, of nuclear matrix proteins from human lung (black circles) and adrenal cortex (white circles) where proteins common to both are shown as half black circles; and FIGS. [2a, 2a', 2b] *2C* and [2b'] *2D* are a comparision of two dimensional electropherograms (pI vs. m.w.), both actual and diagrammatic, of nuclear matrix proteins from human colon (black circles) and bladder (white circles), where proteins common to both are shown as half black circles.

DETAILED DESCRIPTION OF THE INVENTION

The present invention is a method for isolating and identifying nuclear matrix proteins and nuclear matrix associated DNA unique to specific cells of a particular tissue type, some of which are altered by malignancy, viral or bacterial infection, or genetic defect. The sequential extraction yields subfractions of biochemically distinct cellular proteins and DNA as well as morphologically distinct nuclear matrix structures.

In one embodiment of the invention, the nuclear matrix is purified from a cell suspension prepared from a tissue biopsy or blood sample, separated into its "interior" and "exterior" fractions, and then analyzed by two-dimensional gel electrophoresis. Prior to the present invention, no one has been able to separate these fractions nor to extract the nuclear matrix proteins in a way which did not cause extensive degradation. The nuclear matrix proteins account for less than approximately five percent of the total cell protein. Many of the nuclear matrix proteins change when cells are transformed to malignancy. The "interior" proteins represent less than one percent of the total protein, with the "exterior" or "intermediate filament" proteins making up the remainder. The designations "interior" and "exterior" are somewhat arbitrary but in general refer to the localization of the proteins within the nucleus. The interior matrix proteins reflect the structure and composition of the cell being examined. The exterior matrix proteins, by virtue of containing the intermediate filaments, reflect the class of the cell being examined (neuronal, epithelial, etc.).

Separating the exterior proteins from the interior matrix proteins has two important benefits. One, the sensitivity and specificity with which the interior matrix proteins can be identified is greatly enhanced since the exterior matrix proteins amount to greater than one-half of the total protein of the fraction and their presence can obscure less abundant but important interior matrix proteins. Secondly, while inadequate for the purpose of determining tissue type, the exterior proteins themselves provide two analytic tools. The intermediate filament proteins are useful for quick identification of the class of cell being analyzed and the intermediate filament-associated proteins can assist in the identification of disease.

Proteins isolated using the procedure of the present invention are useful as immunogens for the preparation of antibodies when these antibodies are conjugated with colorimetric, immunological (such as labeled anti-antibody), fluorescent, enzymatic or radioactive labels, they can be used as cytological stains on histological sections or for analysis of body fluids and proteins separated by two dimensional gel electrophoresis to provide useful diagnostic information. The antibodies can detect the presence of tumor or viral antigens, abnormal proteins or the absence thereof due, for example, to a defective chromosome or genetic deficiency, and proteins released during cell destruction, as in some types of infection, myocardial infarction, and autoimmune diseases. Antibodies labeled with radioactive material, nuclear magnetic resonance contrast agents, or boron or boron compounds are particularly useful for diagnostic imaging (detection or monitoring) or treatment of various diseases. Antibodies with biologically active agents, including drugs, biological modifiers, angiogenesis or anti-angiogenesis factors, can be used to deliver the agent to a selected location within an individual at a faster rate and higher efficacy of delivery than compounds delivered by presently known methods.

These nuclear matrix proteins are also useful in directly comparing the efficacy of a number of compounds as candidates for treatment of a specific disease (drug screening). For example, steroids appear to bind to the nuclear matrix via some nuclear matrix receptor mechanism. Binding of estrogen or phenol red can stimulate cell proliferation. Binding to the nuclear matrix receptors or proteins seems to modulate specific gene expression. Drugs which interact with and affect the nuclear matrix may have a number of therapeutic applications. The present invention provides a means for comparing the effects of these drugs. The nuclear matrix proteins are isolated, as previously described, exposed to the compound to be tested, and the presence of binding measured. Binding assays are well known to those skilled in the art. Once a compound is found to bind in vitro, it may be tested in vivo for a specific effect on gene expression, proliferation or inhibition. However, the advantage of a rapid, in vitro assay is obvious—only those drugs which bind need to undergo further testing.

The nuclear matrix associated DNA extracted by this procedure has similar uses. The procedures for isolating the interior and exterior nuclear matrix proteins and nuclear matrix associated DNA are as follows:

Cell Preparation

The procedure employs single cells in a suspension. Cells in blood samples or from cell culture are already separate. Tissues obtained by biopsy are dispersed by mild mechanical homogenization followed by digestion with a proteolytic enzyme such as collagenase or trypsin. These enzymes digest connective fibers between cells without affecting the interior contents. In some cases it is desirable to perform an initial, partial separation of cell types. A rapid cell separation is effected by centrifugation, an inert density gradient, or by other means for rapidly separating cells without chemical interaction.

Purification of the Nuclear Matrix Proteins and Associated DNA

The nuclear matrix is separated from other cell constituents by a series of sequential extractions. The cell suspension is exposed to the extraction solution for one to two minutes and then the insoluble material separated by centrifugation (approximately one to two minutes at 1000 g), filtration (pore size approximately 5 microns), or other method known to those skilled in the art. The sequential fractionation is shown schematically in FIG. 1. One key feature of this extraction process is that harsh extraction solvents such as 2M NaCl are avoided. A second is the use of urea or other suitable solubilizing agent to dissolve the interior and exterior proteins, followed by repolymerization of the exterior proteins. The steps are as follows:

1. Removal of soluble cell proteins

The soluble proteins 14, amounting to 70% of the cell mass, are removed by extracting the intact cell 10 with a non-ionic detergent solution 12, such as 0.5% Triton X-100. The non-ionic detergent in a buffer at physiological pH and ionic strength extracts first the membrane lipids and then the soluble proteins. The detergent solubilizes lipids without denaturing proteins and thus avoids disturbing the integrity of the cell structures. The physiological salt solution is essential to maintain the morphology of the cytostructure and to prevent the removal of structural elements. An example of a useful buffer is 100 mM NaCl, 300 mM sucrose, 10 mM pIPES [pH 6.8], 3 mM $MgCl_2$, 0.5% Triton X-100, 1.2 phenylmethylsufonylfluoride at 0° C.

Two diminsional gel analysis of the soluble fraction reveals a complex, dense pattern of major proteins. While many proteins appear to be unique in this fraction, the density of protein spots on the gel precludes more precise analysis.

The remaining skeletal framework, usually masked in conventional Epon-embedded thin section, can be visualized in three dimensions as an unembedded whole mount using the method of Fey et al., in the J. Cell Biol., 98,1973–1984 (1984). For scanning electron microscopy, cells are grown on glass cover slips and fractionated using the method of the present invention. Cells are fixed at various stages of fractionation in the appropriate buffer containing 2.5% gluteraldehyde at 0° C. for 30 minutes followed by rinsing in 0.1M sodium cacodylate and then 1% $OsO_4$ in 0.1M Na cacodylate for 5 minutes at 0° C. The cells, still on coverslips, are dehydrated through an ethanol series, dried through the $CO_2$ critical point and sputter-coated with gold-palladium. The samples are examined in the lower stage of a scanning electron microscope. Transmission electron microscopy is done on cells grown on mold grids which were previously covered with formvar and coated with carbon. Cells are fixed in 2.5% gluteraldehyde and processed as above.

2. Removal of cytoskeleton proteins

The cytoskeleton proteins 20, consisting of the dense cytoplasmic filament networks, intercellular junctional complexes and apical microcellular structures, are next separated from the nucleus by selective solubilization of the cytoskeleton proteins amounting to 20% of cell protein mass, with either a 0.25M ammonium sulfate solution 16 buffered to pH 6.8, for example, 0.25M ammonium sulfate, 0.3M sucrose, 10 mM PIPES [pH 6.8], phenylmethylsulfonyl fluoride, 0.5% Triton X-100, or with a 1% Tween-40, 0.5% sodium deoxycholate solution 18. The nucleus with all of the intermediate filaments still attached, amounting to about 5% of the total cellular protein, remains.

3. Removal of the chromatin proteins

The chromatin proteins 26, whose association with the nucleus depends on the integrity of DNA and RNA, is next separated from the nuclear matrix. The nucleus is first digested with DNAase and RNAase in near physiological digestion buffer 22, for example, 50 mM NaCl, 0.3M sucrose, 10 mM PIPES [pH 6.8], 3 mM $MgCl_2$, 0.5% Triton X-100, 1.2 mM phenylmethylsulfonyl fluoride with 100 micrograms bovine pancreatic DNAase (EC 3.1.4.5, Worthington Biochemical Corp., Freehold, N.J.) and 100 micrograms/ml pancreatic RNAse A (EC 3.1.4.22., Sigma Chemical Co., St. Louis, Mo.). The enzyme cuts DNA principally between the basic units of chromatin or nucleosomes. At this stage, the DNA remains completely in the nucleus in the form of individual nucleosomes. The DNA-containing nucleosomes are then eluted for approximately 5 minutes at 20° C. using 0.25M ammonium sulfate buffered to pH 6.8 24. Although 0.25M ammonium sulfate is preferred, comparable buffers could be used.

4. Separation of the Interior and Exterior Proteins of the Matrix

The nuclear matrix consists of less than 5% of the cell protein mass.

The nuclear matrix is further divided into two distinct parts, termed the interior and exterior (or intermediate filaments). The exterior part consists of the intermediate filaments and intermediate filament associated proteins. Although the filaments are exterior to the matrix, in the cytoplasm, they are physically connected to the nuclear surface and behave physiologically as part of the nuclear matrix. They and their associated proteins amount to greater than one-half of the proteins in the matrix preparation.

Fractions selectively enriched in the interior and exterior matrix proteins are produced by completely dissolving the matrix proteins in a buffered 5 to 10M urea solution 28 preferably 8M, or other suitable solubilizing agent such as, for example, lithium diiodosalicylate, as required to completely dissolve the nuclear matrix proteins, and then dialyzing the proteins back into physiological buffer 30. The interior proteins 32 remain in solution. The intermediate filament proteins and associated proteins reassemble into large insoluble filaments 34 during dialysis to remove the solubilizing agent. The urea or comparable solubilizing agent is essential for dissolving the proteins, which are generally quite insoluble. Removal of the solubilizing agent, as by dialysis, is essential to reform and separate out the intermediate filament fractions.

In a variation of the method for isolating the nuclear matrix proteins described above, the cytoskeleton proteins 20 and chromatin 26 are removed together. The soluble proteins 14 are first removed by extraction with a non-ionic detergent buffered solution 12. The insoluble material is digested with DNAase and RNAase in a buffered solution 22 then the cytoskeleton proteins 20 and chromatin 26 extracted with 0.25M ammonium sulfate at physiological pH 28.

The selectively enriched fractions can be further separated by electrophoresis, "chromatofocusing" (BioRad Laboratories, Richmond, Calif.), HPLC and related technologies such as FPLC (fast protein liquid chromatography), isoelectrofocusing, and conventional ion exchange or affinity chromatography. Once specific proteins are separated, the proteins can be used to make monoclonal antibodies which can be bound to matrices for use in purification of additional protein, as well as in analysis.

Protein Analysis

The highly purified matrix proteins are analyzed using conventional two-dimensional acrylamide gel electrophoresis. The proteins are first separated in a pH gradient gel according to electrophoretic mobility or isoelectric point. This gel is then placed on a standard 10% acrylamide slab gel and the proteins separated according to molecular weight. One method of two dimensional gel electrophoresis is taught by P.H. O'Farrell in J. Biol. Chem. 250, 4007–4021 (1975) using an ampholyte gradient consisting of 90% pH 5–7 (0.4% ampholyte) and 10% pH 3–10 (1.6% ampholyte). The proteins form a pattern of spots, made detectable by silver staining or by autoradiography, which is diagnostic of the cell type and state of transformation or abnormalities. Equivalent $^{35}S$ cpm can be used to facilitate qualitative comparisons.

Immunoblot electrophoresis can also be used to identify proteins in the nuclear matrix - intermediate filament scaffold fraction, including vimentin, cytokeratins desmosomal proteins, and specific nuclear matrix proteins. The procedure for immunoblot electrophoresis is as follows. One-dimensional polyacrylamide gels are run according to the method of Laemmli in Nature (Lond.), 227,680–685 (1970). Equal protein concentrations are loaded to compare individual fractions. The reaction of antibodies to protein bands are visualized on nitrocellulose paper according to the procedure of H. Towbin et al., Proc. Natl. Acad. Sci. U.S.A., 76,4350–4354 (1979). Nitrocellulose strips are incubated for 12 hours in 2% hemoglobin in PBS, rinsed three times in PBS, and incubated for 2 hours at 20° C. with antibody to the protein to be detected at the appropriate concentration. Excess antibody is removed by washing with PBS (four 20 minute washes). The strips are then incubated with goat anti-rabbit (or anti-mouse) IgG conjugated to horseradish peroxidase, washed in PBS (four times for a total of 80 minutes) and then developed in 0.4 mg/ml 4-chloro-1-napthol in 0.01% (vol/vol) $H_2O_2$ using the technique of R. Hawkes et al., in Anal. Biochem., 119,142–147 (1982).

The matrix preparation is biochemically and morphologically pure by several biochemical criteria. It retains most matrix specific constituents. Freedom from contamination permits a clear and detailed analysis of the matrix proteins by gel electrophoresis.

As shown in FIG. 1, nuclear matrix associated DNA 44 is isolated from the intact cell 10 by extraction of the soluble proteins 14 with a non-ionic detergent in a physiological buffered solution 12, solubilization of the chromatin 26 and cytoskeleton proteins 20 by digestion with DNAase in a physiological buffer 36 followed by extraction into 0.25M ammonium sulfate at physiological pH 24, and removal of any remaining protein 42 by phenol extraction 38, centrifugation in a cesium chloride gradient 40 or other method known to those skilled in the art. Digestion of the insoluble material with DNAase 36 instead of DNAase in combination with RNAase 22 results in the removal of approximately 94% of the cell DNA instead of approximately 98%.

In another embodiment of this procedure, also shown in FIG. 1, fragments of nuclear matrix associated DNA 48 are prepared by digestion of the insoluble cell material remaining after extraction of the soluble proteins 14 with one or more restriction endonucleases in the appropriate buffer 46, followed by extraction of the cytoskeleton proteins 20 and chromatin 26 in 0.25M ammonium sulfate at physiological pH 24 and removal of any remaining protein 42 by phenol extraction 38, cesium chloride centrifugation 40, or other method known to those skilled in the art.

The two dimensional gel electrophoresis and other purification techniques yield pure proteins for use in the production of antibodies. Polyclonal or monoclonal antibodies may be preferred, depending on the antigen to be detected and the technique utilized. Monoclonal antibodies are secreted by hybridoma cell lines produced by established immunization and fusion protocols known to those skilled in the art, such as the method of G. Galfre et al., in Nature (Lond.) 266,550–552 (1977).

Cell type specficity of matrix proteins has been demonstrated using laboratory cultured cell lines. These include common laboratory lines such as primary and established fibroblasts, HeLa cells, etc. Most relevant to clinical applications are the results from a number of carcinoma lines derived from human biopsy material. As shown in FIGS. [2b] *2C* and [2b'] *2D* these include human colon, lung, adrenal cortex and bladder cell lines. Although the electropherogram patterns are markedly different in different cell types, each cell type containing unique as well as common proteins, the pattern for each cell type is specific and reproducible. Similar results can be obtained with animal tissue, having been demonstrated using mouse tissue.

In addition to identifying the tissue of origin of the nuclear matrix proteins, the matrix protein patterns reflect cell transformation, viral infection, and genetic defects. This has been demonstrated in spontaneous transformation of rodent primary fibroblasts, viral transformation of established rodent fibroblasts, transformation of a kidney cell line by transaction with the ras oncogene, and transformation of a kidney cell line by the ultimate carcinogen, BAP diole epoxide, using a number of cloned cell lines in each case. Each showed different and marked variation in their matrix protein pattern, but retained sufficient information to determine the cell of origin.

The type and degree of transformation or infection are also closely correlated with changes in matrix protein composition. Of particular interest are the qualitative differences between transformation by the complete carcinogen and by ras gene transfection. Six cloned isolates of cells transformed by ras transfection and 10 isolates of the carcinogen-transformed cells were analyzed. A brief summary of the results is:

a. Transformation by chemical carcinogen leads to the appearance in the matrix of 12 to 15 new or previously undetected proteins.

b. Transfection by the ras gene results in the loss of about 6 proteins and, in some cases, the appearance of 2 or 3 new proteins. There appears to be a correlation between the degree of morphological aberrance and the number of matrix protein changes.

The data from transformed cells reveals different types of transformation events with characteristic signatures.

Analysis of the nuclear matrix associated DNA provides further information for determining the cell type, tissue of origin, and degree of abnormality of cells. "Actively" transcribed DNA in a cell is usually associated with the nuclear matrix proteins. This DNA represents approximately 6% of the total cell DNA. Approximately one-third (2% of total DNA) is directly bound to the protein portion of the matrix and approximately two-thirds (4% of the total DNA) is bound to the RNA component of the nuclear matrix. Different quantities of DNA as well as specific sequences of DNA will be associated with the nuclear matrix and nuclear matrix proteins, depending on cell type and whether the cell is abnormal and to what degree the cell is abnormal. The isolated DNA can be analyzed and identified using gel electrophoresis and blot hybridization with probes specific for a particular unique sequence or repetitive sequence. Probes may be made by inserting the sequence of interest, either a synthetic sequence or a portion of the gene of interest, into a recombinant plasmid using methods known to those skilled in the art. [The probes can be used to screen commercially available libraries, such as the λGT11 library, for cDNA encoding nuclear matrix proteins. The library could also be screened using antibodies to the proteins.] The probes can [also] be conjugated with a radiolabel, biotinylated, or crosslinked with psoralin and derivaties thereof for use as a double stranded probe, and used in assays, imaging, isolation and identification procedures. 5

[The isolated DNA can be inserted into a vector for expression of nuclear matrix proteins or expressed directly in a system such as one of the frog oocytes direct expression systems.]

Analysis of either the proteins or the DNA provides a means to determine the presence of chromosomal defects or genetic deficiencies which might otherwise be undetectable. One application is in the analysis of cells obtained by amniocentesis. Another is in the identification and assessment of autoimmune diseases. Both the antibodies and hybridization probes can be used to analyze cellular materials and body fluids, both in vivo (tissue imaging) and in vitro, for nuclear matrix proteins. However, steps to concentrate or enhance the antigen levels in the body fluids may be required to insure adequate levels for detection. Once probes or antibodies are developed, for example, to carcinoma specific proteins, they can be labeled and used to rapidly screen either histological sections such as a pap smear, or the body fluid.

The extremely rapid, simple extraction and analytical procedure of the present invention provides a means for an objective determination of the tissue of origin of normal and abnormal cells and their degradation products, thereby indicating whether transformation or infection of normal cells has occurred, whether there has been metastasis and to what degree, and whether the individual has any autoimmune disease.

Although this invention has been described with reference to specific embodiments, variations and modifications of the method for isolating and diagnosing nuclear matrix proteins and associated DNA from cells of unknown tissue type or state of malignancy, infection or abnormality will be obvious to those skilled in the art. It is intended that such modifications and variations fall within the scope of the appended claims.

What is claimed is:

1. A method for characterizing the origin and malignancy of cellular materials comprising:

(a) isolating interior nuclear matrix proteins from at least one type of cell of known origin;

(b) separating the isolated interior nuclear matrix proteins;

(c) comparing isolated and separated interior nuclear matrix proteins from cells of unknown origin with the separated interior nuclear matrix proteins of known origin; and (d) characterizing interior nuclear matrix proteins from cells of unknown origin based upon the comparison with interior nuclear matrix proteins from cells of known origin.

2. The method of claim 1 further comprising (a) isolating interior nuclear matrix proteins from cells of unknown origin; and (b) separating the isolated nuclear matrix proteins from cells of unknown origin;

wherein the isolated and separated nuclear matrix proteins from cells of unknown origin are then compared and characterized according to steps (c) and (d) of claim 1.

3. The method of claim 1 *or 2* wherein the interior nuclear matrix proteins are isolated by:

(a) extracting eucaryotic cells with a non-ionic detergent solution at physiological pH and ionic strength to extract the proteins in the nucleus and cytoskeleton which are soluble in the physiological detergent solution;

(b) separating the nuclear matrix proteins from the cytoskeleton proteins remaining in the extracted cells of step *(a)* by solubilizing the cytoskeleton proteins in a solution which does not dissolve the nuclear proteins;

(c) separating the chromatin proteins from the nuclear matrix by digesting the insoluble material from step *(b)* with DNAase and RNAase and dissolving the chromatin proteins with a buffered ammonium sulfate solution;

(d) separating the interior and exterior proteins of the nuclear matrix by first dissolving the insoluble nuclear matrix proteins from step *(c)* in a solubilizing agent and then dialyzing the dissolved proteins back into a physiological buffer, wherein the interior nuclear matrix proteins are soluble in the physiological buffer and the exterior nuclear matrix proteins are insoluble.

4. The method of claim [1] *3* wherein the solubilizing agent in step (d) is urea.

5. The method of claim 1 further comprising purifying the exterior nuclear matrix proteins from cells of known origin and degree of malignancy.

6. The method of claim [2] *3* wherein cytoskeleton proteins and chromotin proteins [in the extract of step a] are removed together from the nuclear matrix proteins by digesting the non-extracted material from step *(a)* with DNAase and RNAase.

7. The method of claim 1 *or 2* further comprising isolating nucleic acids associated with the interior nuclear matrix proteins isolated in step *(a)* [from at least one cell of known origin].

8. The method of claim 7 further comprising making [antibodies or] hybridization probes to [the isolated, separated interior nuclear matrix proteins of step (b) and] *said* nucleic acids [associated with the interior nuclear matrix proteins of step (a)].

9. The method of claim 8 further comprising

*(a)* labeling [the antibodies to the interior nuclear matrix proteins or] *said* hybridization probes [to nucleic acids associated with the interior nuclear matrix proteins and comparing the interior nuclear matrix proteins and associated nucleic acids from cells of unknown origin by reacting the proteins and nucleic acids with the labeled antibodies and hybridization probes to interior nuclear matrix proteins and];

*(b) detecting interior nuclear matrix protein associated nucleic acids with said labeled hybridization probes; and*

*(c) comparing said detected nucleic acids with interior nuclear matrix* associated nucleic acids of known origin.

10. The method of claim 7 further comprising digesting the nuclear matrix associated nucleic acids with restriction enzymes.

11. The method of claim 7 wherein the nuclear matrix associated nucleic acids are isolated by:

(a) extracting eucaryotic cells with a non-ionic detergent solution at physiological pH and ionic strength to extract the proteins in the nucleus and cytoskeleton which are soluble in the physiological detergent solution;

(b) digesting the non-extracted material from step *(a)* with DNAase and then dissolving the digested extracted material into a buffered ammonium sulfate solution; and (c) removing any remaining protein from the material in step *(b)* which does not dissolve in the buffered ammonium sulfate solution using a method which does not denature or remove nucleic acids.

12. The method of claim 1 further comprising selecting the cells of known origin of step a from the group of cells consisting of normal cells, cells containing nucleotide sequences of viral origin or proteins derived thereof, malignant cells, and cells having chromosomal deficiencies or defects for the production of specific proteins.

13. A method for detecting *cell type-specific* interior [and exterior] nuclear matrix proteins [and associated nucleic acids] in [samples] *a sample* of cellular material [and] *or* body [fluids] *fluid, said method* comprising:

(a) reacting *the sample to be analyzed with* labeled antibodies to isolated *cell type-specific* interior [and exterior] nuclear matrix proteins of known origin [with the samples to be analyzes]; and (b) detecting the presence *in the sample* of proteins recognized by *said labeled* antibodies [to the interior and exterior nuclear matrix proteins from cells of known origin in the samples of cellular material or body fluid], *said isolated cell type-specific interior nuclear matrix proteins being characterized as non-cytoskeletal, non-lamin, non-chromatin protein isolated from mammalian nuclei, resistant to solubilization from said nuclei in 0.25M ammonium sulfate, remaining in solution following dialysis into physiological buffer from 8M urea, and segregating into a reproducible pattern unique to a given cell type on a two-dimensional electrophoresis gel.*

14. A method for detecting *cell type-specific interior* nuclear matrix *protein* associated nucleic acids in [samples] *a sample* of cellular material [and] *or a* body [fluids] *fluid, said method* comprising:

(a) reacting *the sample to be analyzed with* labeled hybridization probes to *isolated, cell type-specific* interior [and exterior] nuclear matrix protein associated nucleic acids of known origin [with the sample to be analyzed]; and (b) detecting the presence *in the sample* of nucleic acids recognized by *said labeled* hybridization probes [to nucleic acids associated with either interior or exterior nuclear matrix proteins from cells of known origin in the samples of cellular material or body fluid], *said isolated cell type-specific interior nuclear matrix protein associated nucleic acids being characterized as co-purifying with non-cytoskeletal, non-lamin, non-chromatin protein isolated from mammalian nuclei, being resistant to nuclease digestion during isolation from said nucleic, and segregating into a reproducible pattern unique to a given cell type when digested with restriction endonuclease and separated by gel electrophoresis, said co-purifying protein being resistant to solubilization from said nuclei in 0.25M ammo-*

*nium sulfate, remaining in solution following dialysis into physiological buffer from 8M urea, and segregating into a reproducible pattern unique to a given cell type on a two-dimensional electrophoresis gel.*

15. A method for detecting chemical compounds which bind *cell type-specific interior* nuclear matrix proteins [or nuclear matrix associated nucleic acids] comprising (a) reacting selected compounds with isolated, *cell type-specific* interior [and exterior] nuclear matrix proteins [or nucleic acids associated with either interior or exterior nuclear matrix protein], *said isolated cell type-specific interior nuclear matrix proteins being characterized as non-cytoskeletal, non-lamin, non-chromatin protein isolated from mammalian nuclei, resistant to solubilization from said nuclei in 0.25M ammonium sulfate, remaining in solution following dialysis into physiological buffer from 8M urea, and segregating into a reproducible pattern unique to a given cell type on a two-dimensional electrophoresis gel*;

(b) detecting the presence of binding between the compound and [the] *a said* isolated *cell type-specific* interior [or exterior] nuclear matrix protein [or associated nucleic acid]; and (c) determining the extent of binding.

16. [Interior] *A cell type-specific* nuclear matrix [proteins] *protein* isolated from [eucaryotic cells] *transformed mammalian cell nucleic of known origin selected from the group consisting of lung, adrenal cortex, colon, bladder and kidney cells* by:

(a) extracting eucaryotic cells with a non-ionic detergent-salt solution at physiological pH and ionic strength to extract the proteins in the nucleus and cytoskeleton which are soluble in the physiological detergent solution;

(b) separating the nuclear matrix proteins from the cytoskeleton remaining in the extracted cells of step *(a)* by solubilizing the cytoskeleton proteins in a solution which does not dissolve the nuclear matrix proteins;

(c) separating the chromatin proteins from the nuclear matrix proteins by digesting the insoluble material from step *(b)* with DNAase and RNAase and dissolving the chromatin in a buffered ammonium sulfate solution; and (d) separating the interior and exterior proteins of the nuclear matrix by dissolving the insoluble nuclear matrix proteins from step *(c)* in a solubilizing agent and dialyzing the dissolved proteins back into a physiological buffer, wherein the interior nuclear matrix proteins are soluble in the physiological buffer and the exterior nuclear matrix proteins are insoluble and removing the insoluble exterior matrix proteins from the solution, *said isolated, cell type-specific interior nuclear matrix protein being characterized as non-cytoskeletal, non-lamin, non-chromatin protein present in the nuclei of said transformed cells, having an isoelectric point of at least 4.0 and not greater than 8.0 and being detectable on a two dimensional electrophoresis gel, said protein not being detectable on said two-dimensional electrophoresis gel from normal cells of said known origin.*

17. [Antibodies] *Isolated antibodies* to the *isolated cell type-specific* interior nuclear matrix proteins of claim 16.

[18. cDNA and derivatives thereof encoding the isolated interior nuclear matrix proteins of claim 16.]

[19. Interior nuclear matrix protein associated nucleic acids isolated from eucaryotic cells by (a) separating the soluble proteins from the nucleus and cytoskeleton by extracting eucaryotic cells with a non-ionic detergent solution at physiological pH and ionic strength;

(b) digesting the insoluble protein and nucleic acid from step a with DNAase and then eluting with a buffered ammonium sulfate solution to yield nucleic acids associated with nuclear matrix proteins;

(c) separating the nucleic acids associated with interior nuclear matrix proteins from the nucleic acids associated with the exterior nuclear matrix proteins; and (d) removing any remaining protein from the separated insoluble interior nuclear matrix protein associated nucleic acids and exterior nuclear matrix protein associated nucleic acids from step c.]

[20. Hybridization probes derived from the interior nuclear matrix protein associated nucleic acids and exterior nuclear matrix protein associated nucleic acids of step c of claim 19.]

[21. Restriction fragments of nuclear matrix associated nucleic acid prepared by (a) separating the soluble proteins from the nucleus and cytoskeleton by extracting eucaryotic cells with a non-ionic detergent solution at physiological pH and ionic strength;

(b) digesting the insoluble protein and nucleic acid from step a with one or more restriction enzymes in the appropriate buffer and then eluting with a buffered ammonium sulfate solution to yield restriction fragments of nucleic acids associated with nuclear matrix proteins;

(c) separating the nucleic acids associated with interior nuclear matrix proteins from the nucleic acids associated with the exterior nuclear matrix proteins; and (d) removing any remaining protein from the separated insoluble interior nuclear matrix protein associated nucleic acids and exterior nuclear matrix protein associated nucleic acids from step c.]

*22. The method of claim 1 or 2 further comprising making antibodies to the isolated interior nuclear matrix proteins of step (a) or (b).*

*23. The method of claim 22 further comprising*

*(a) labelling said antibodies*

*(b) detecting interior nuclear matrix proteins from cells of unknown origin with said labeled antibodies; and*

*(c) comparing said detected proteins with interior nuclear matrix proteins of known origin.*

*24. The method of claim 13 wherein said proteins detected are released from cells as degradation products.*

*25. The method of claim 14 wherein said nucleic acids detected are released from cells as degradation products.*

*26. An isolated cell type-specific interior nuclear matrix protein, said protein being characterized as non-cytoskeletal, non-lamin, non-chromatin protein present in the nuclei of transformed mammalian cells of known origin and selected from the group consisting of lung, colon, adrenal cortex, bladder and kidney cells, resistant to solubilization from said nuclei in 0.25M ammonium sulfate, remaining in solution following dialysis into physiological buffer from 8M urea, having an isoelectric point of at least 4.0 and not greater than 8.0 and being detectable on a two dimensional electrophoresis gel, said protein not being detectable on said two dimensional eletrophoresis gel from normal cells of said known origin.*

*27. Isolated antibodies to the isolated cell type-specific interior nuclear matrix proteins of claim 26.*

* * * * *